(12) United States Patent
Reddy et al.

(10) Patent No.: US 11,305,074 B2
(45) Date of Patent: Apr. 19, 2022

(54) INSUFFLATION SYSTEM (71) Applicant: BIOGASTREX LLC, Tuscaloosa, AL (US)

(72) Inventors: Adisesha Reddy, Tuscaloosa, AL (US); Juan Carrasquilla, Tuscaloosa, AL (US)

(73) Assignee: BIOGASTREX LLC, Tuscaloosa, AL (US)

( * ) Notice: Subject to any disclaimer, the term of this patent is extended or adjusted under 35 U.S.C. 154(b) by 0 days.

(21) Appl. No.: 16/495,210

(22) PCT Filed: Jan. 23, 2019

(86) PCT No.: PCT/US2019/014735
§ 371 (c)(1),
(2) Date: Sep. 18, 2019

(87) PCT Pub. No.: WO2019/147659
PCT Pub. Date: Aug. 1, 2019

(65) Prior Publication Data
US 2021/0008301 A1 Jan. 14, 2021

Related U.S. Application Data

(60) Provisional application No. 62/712,004, filed on Jul. 30, 2018, provisional application No. 62/621,629, filed on Jan. 25, 2018.

(51) Int. Cl.
*A61M 13/00* (2006.01)
*A61B 1/00* (2006.01)

(52) U.S. Cl.
CPC ....... *A61M 13/003* (2013.01); *A61B 1/00068* (2013.01); *A61B 1/00114* (2013.01); *A61B 1/00119* (2013.01); *A61M 2202/0225* (2013.01); *A61M 2205/3334* (2013.01); *A61M 2205/3592* (2013.01); *A61M 2205/581* (2013.01); *A61M 2205/583* (2013.01); *A61M 2205/587* (2013.01)

(58) Field of Classification Search
CPC ........ A61M 13/003; A61M 2202/0225; A61M 2205/581; A61M 2205/587;
(Continued)

(56) References Cited

U.S. PATENT DOCUMENTS 5,304,129 A * 4/1994 Forgach .................. A61M 1/82
604/74
5,322,506 A 6/1994 Kullas
(Continued)

FOREIGN PATENT DOCUMENTS

WO 2014117265 8/2014
WO 2017048194 3/2017

OTHER PUBLICATIONS

International Search Report and Written Opinion dated Jun. 11, 2019, from International Application No. PCT/US2019/014735, 13 pages.

*Primary Examiner* — Amber R Stiles
*Assistant Examiner* — Avery Smale
(74) *Attorney, Agent, or Firm* — Meunier Carlin & Curfman LLC (57) ABSTRACT

Various implementations include an insufflation system for use with an endoscope. The insufflation system includes a housing, a $CO_2$ system, a water system, a foot pedal, a control system, an aromatic dispersion system, an audio system, and a water tubing valve. Various implementations also include a more visible foot pedal, which is useful in difficult-to-see environments. In some implementations, a water tubing valve couples conduits from two water containers to the endoscope. In a first position, water flows only from a first water container. In a second position, water flows only from a second water container. The water tubing valve prevents water-flow from both of the first water container and the second water container to happen simultaneously. The water tubing valve allows for an operator to quickly (Continued)

switch a source of the water, thereby facilitating continuation of a procedure in a case that the first water container is fully depleted.

19 Claims, 8 Drawing Sheets

(58) Field of Classification Search
CPC ........ A61M 2205/078; A61M 2205/59; A61M 13/006; A61M 2202/04; A61M 2205/588; A61M 2205/3334; A61M 39/223; A61B 1/00068; A61B 1/00119; A61L 9/03
See application file for complete search history.

(56) References Cited

U.S. PATENT DOCUMENTS

| | | | |
|---|---|---|---|
| 5,800,381 A | 9/1998 | Ognier | |
| 6,126,592 A | 10/2000 | Proch et al. | |
| 2001/0025167 A1* | 9/2001 | Kraus | A61M 39/28 604/410 |
| 2004/0102731 A1* | 5/2004 | Blackhurst | A61M 16/08 604/26 |
| 2006/0090990 A1 | 5/2006 | Blaha et al. | |
| 2007/0043262 A1* | 2/2007 | Levy | A61B 1/00068 600/156 |
| 2007/0265492 A1 | 11/2007 | Sonnenschein et al. | |
| 2012/0048264 A1* | 3/2012 | Finlay | A61M 13/003 128/200.14 |
| 2012/0197084 A1 | 8/2012 | Drach et al. | |

* cited by examiner

INSUFFLATION SYSTEM

CROSS REFERENCE TO RELATED APPLICATIONS

This application is a National Stage Application of International Application No. PCT/US2019/014735, entitled "INSUFFLATION SYSTEM," filed Jan. 23, 2019, which claims priority to U.S. Provisional Application Nos. 62/621,629, entitled "CO2 INSUFFLATION SYSTEM FOR GASTROINTESTINAL ENDOSCOPY," filed Jan. 25, 2018, and U.S. Provisional Application No. 62/712,004, entitled "CO2 INSUFFLATION SYSTEM FOR GASTROINTESTINAL ENDOSCOPY," filed Jul. 30, 2018, the contents of which are herein incorporated by reference in their entirety.

BACKGROUND

Previous insufflation systems have been developed to provide $CO_2$, water, or both to an endoscope. However, current systems provide the $CO_2$ and water from separate housings. This lack of consolidation is an inconvenience for physicians. In addition, current systems allow for only one water bottle to be connected to the endoscope. A procedure must be stopped if the water bottle runs out of water in order to replace the water bottle. Thus, there is a need in the art for uninterrupted water flushing during a colonoscopy procedure so that the endoscopist can focus on identifying the pathology without undue distraction and interruption.

Furthermore, some of these systems utilize hands free operation, such as foot pedals, to control the flow of water to the endoscope. Current foot pedals are simple, normally-open buttons covered with rubber padding and connected to the insufflation system with a wire. When pressed, the button closes the circuit which operates the pump and triggers a flow of water. However, the room in which endoscopy is being conducted is often a low lighting environment, making it difficult for the operator to locate the foot pedal. Thus, there is a need in the art for a more visible foot pedal.

Moreover, the room in which the endoscopy is being conducted is often filled with unpleasant odors due to the procedure. Thus, there is a need for improved infusion devices for GI endoscopy.

SUMMARY

Various implementations include an insufflation system including a housing, a $CO_2$ conduit, an endoscope water pump, and a water pump. The housing defines an inlet $CO_2$ port and an outlet $CO_2$ port. The $CO_2$ conduit is disposed within the housing and couples the inlet and outlet $CO_2$ ports. The endoscope water pump is coupled to the housing. The foot pedal is coupled to a control system. The control system is electrically coupled to the endoscope water pump and the housing. The foot pedal being compressible. Compression of the foot pedal causes generation of an electrical signal that causes the endoscope water pump to turn on or off. The foot pedal has an outer surface that is at least partially illuminated.

In some implementations, the insufflation system includes a $CO_2$ source coupled to the inlet $CO_2$ port for providing $CO_2$ to the inlet $CO_2$ port.

In some implementations, the insufflation system includes a water container coupled to the housing.

In some implementations, the insufflation system includes an endoscope coupled to the $CO_2$ source and the water container. The endoscope is coupled to the $CO_2$ source via the inlet and outlet $CO_2$ ports and $CO_2$ conduit. The endoscope is coupled to the water container via a water conduit. The water conduit extends through the endoscope water pump.

In some implementations, the insufflation system includes a $CO_2$ valve and at least one circuit board. The $CO_2$ valve is in fluid communication with the outlet $CO_2$ port. The at least one circuit board is disposed within the housing. The circuit board is electrically coupled to the $CO_2$ valve and the endoscope water pump to control flow through the $CO_2$ valve and endoscope water pump.

In some implementations, the housing includes at least one face on which one or more control devices are coupled. The control devices are electrically coupled to the circuit board for controlling operation of the $CO_2$ valve or the endoscope water pump or both.

In some implementations, the one or more control devices include a water flow rate control device for selecting a flow rate of the endoscope water pump.

In some implementations, the one or more control devices include a $CO_2$ flow rate control device for selecting a flow rate through the $CO_2$ valve.

In some implementations, the $CO_2$ valve includes a miniature proportional valve to regulate flow of $CO_2$.

In some implementations, the insufflation system includes a $CO_2$ switch electrically coupled to the $CO_2$ valve for providing an on/off signal to the $CO_2$ valve.

In some implementations, the insufflation system includes a timer electrically coupled to the $CO_2$ switch.

In some implementations, the insufflation system includes a water switch electrically coupled to the endoscope water pump for providing an on/off signal to the endoscope water pump.

In some implementations, the insufflation system includes a timer electrically coupled to the water switch.

In some implementations, the housing defines a power port, and a power source is coupled to the circuit board through the power port.

In some implementations, the housing defines an aromatic outlet for coupling with an aromatic dispersion system. The aromatic dispersion system includes an aroma source receptacle and an evaporative diffuser for diffusing the aroma source. The diffused aroma source flows through the aromatic outlet to an environment outside of the housing. In some implementations, at least a portion of the aromatic dispersion system is disposable within the housing. In some implementations, the aroma source is essential oil. In some implementations, the evaporative diffuser includes a heat-sink disposed within the housing for evaporating an aroma source disposed within an absorbent pad.

In some implementations, the insufflation system includes at least one speaker and audio input receiver disposed within the housing. The audio input receiver is for receiving an audio input signal. The audio input receiver is in electrical communication with the at least one speaker, and the audio input signal is output by the speaker. In some implementations, the audio input receiver is in wireless communication with an audio input source to receive the audio input signal. In some implementations, the audio input receiver includes a BLUETOOTH communication device.

In some implementations, the insufflation system includes a trace heating system thermally coupled to the $CO_2$ conduit.

In some implementations, the insufflation system includes a standard luer connector disposed within the outlet $CO_2$ port.

In some implementations, the insufflation system includes a male threaded connector disposed within the inlet $CO_2$ port. In some implementations, the outer surface of the foot pedal includes a phosphorescent material.

In some implementations, the outer surface of the foot pedal includes a transparent or translucent material, and the foot pedal includes a light source that emits visible light through the transparent or translucent material.

In some implementations, the water container holder is capable of holding two or more medical-grade endoscopy water containers.

In some implementations, the $CO_2$ conduit and water conduit are medical-grade tubing.

In some implementations, the $CO_2$ conduit and the water conduit are coupled together using a clip.

In some implementations, the insufflation system includes a valve for selecting a water container from two or more water containers from which water flows to the endoscope. The valve includes a body and a ball. The body has an exterior surface and defines an interior seat having an interior surface, a body outlet port, and at least first and second body inlet ports. The body outlet port and the first and second body inlet ports extend from the exterior surface to the interior surface of the seat. The ball has an outer surface and is disposed within the seat. The ball defines at least a first passage and a second passage therethrough. Each of the first and second passages are arcuate and have a ball inlet and a ball outlet defined by the outer surface of the ball. The ball inlets and ball outlets of each passage are spaced apart from each other. The first and second passages do not intersect. The ball is rotatable within the seat between a first position and a second position. In the first position, the ball inlet of the first passage is aligned with the first body inlet port and the ball outlet of the first passage is aligned with the body outlet port, and the ball inlet of the second passage is not in fluid communication with the second body inlet port. In the second position, the ball inlet of the second passage is aligned with the second body inlet port and the ball outlet of the second passage is aligned with the body outlet, and the ball inlet of the first passage is not in fluid communication with the first body inlet port.

In some implementations, the water container is a first water container and the system includes a second water container. The water conduit includes a first water conduit, a second water conduit, and a third water conduit. The first water conduit couples the first body inlet port to the first water container, the second water conduit couples the second body inlet port to the second water container, and the third water conduit couples the endoscope to the body outlet port.

In some implementations, the ball is coupled to a rotatable switch for toggling the valve between the first and second positions. The switch is disposed external to the exterior surface of the valve.

Various other implementations include a fluid flow switch system including a fluid flow switch and a compressible foot pedal. The fluid flow switch is electrically coupled to a fluid flow valve. The compressible foot pedal has an outer surface, and at least a portion of the outer surface includes a phosphorescent material. The compressible foot pedal is biased toward an expanded position. Compression of the compressible foot pedal to a compressed position causes generation of an electrical signal. The electrical signal causes the fluid flow switch to turn the fluid flow valve on or off.

In some implementations, the compressible foot pedal includes a compressible bladder.

In some implementations, the compressible foot pedal includes a stiff plate that is hingedly coupled to a base plate, and compression of the stiff plate toward the base plate generates the electrical signal.

Various other implementations include a fluid flow switch system including a flow switch, a compressible foot pedal, and a light source. The fluid flow switch is electrically coupled to a fluid flow valve. The compressible foot pedal has an outer surface. At least a portion of the outer surface includes a transparent or translucent material. The compressible foot pedal is biased toward an expanded position. Compression of the compressible foot pedal to a compressed position causes generation of an electrical signal. The electrical signal causes the fluid flow switch to turn the fluid flow valve on or off. The light source is disposed within the compressible foot pedal such that light from the light source exits through the transparent or translucent material of the outer surface.

In some implementations, the compressible foot pedal includes a compressible bladder.

In some implementations, the compressible foot pedal includes a stiff plate that is hingedly coupled to a base plate, and compression of the stiff plate toward the base plate generates the electrical signal.

Various other implementations include an insufflation system including a housing, a $CO_2$ conduit, and an aromatic outlet. The housing defines an inlet $CO_2$ port, an outlet $CO_2$ port, and an endoscope water pump. The outlet $CO_2$ port is for coupling to an endoscope. The $CO_2$ conduit is disposed within the housing that couples the inlet and outlet $CO_2$ ports. The aromatic outlet is defined in the housing. The aromatic outlet is for coupling with an aromatic dispersion system. The aromatic dispersion system includes an aroma source receptacle and an evaporative diffuser for diffusing the aroma source. The diffused aroma source flows through the aromatic outlet to an environment outside of the housing.

In some implementations, at least a portion of the aromatic dispersion system is disposable within the housing.

In some implementations, the aroma source is essential oil.

In some implementations, the evaporative diffuser includes a heatsink disposed within the housing for evaporating an aroma source disposed within an absorbent pad.

In some implementations, the insufflation system includes at least one speaker and an audio input receiver disposed within the housing. The audio input receiver is for receiving an audio input signal. The audio input receiver is in electrical communication with the at least one speaker, and the audio input signal is output by the speaker.

Various other implementations include a valve including a body and a ball. The body has an exterior surface and defines an interior seat having an interior surface, a body outlet port, and at least first and second body inlet ports. The body outlet port and the first and second body inlet ports extend from the exterior surface to the interior surface of the seat. The ball has an outer surface and is disposed within the seat. The ball defines at least a first passage and a second passage therethrough. Each of the first and second passages are arcuate and have a ball inlet and a ball outlet defined by the outer surface of the ball. The ball inlets and ball outlets of each passage are spaced apart from each other. The first and second passages do not intersect. The ball is rotatable within the seat between a first position and a second position. In the first position, the ball inlet of the first passage is aligned with the first body inlet port and the ball outlet of the first passage is aligned with the body outlet port, and the ball inlet of the second passage is not in fluid communication with the second body inlet port. In the second position, the ball inlet of the second passage is aligned with the second body inlet port and the ball outlet of the second passage is aligned with the body outlet, and the ball inlet of the first passage is not in fluid communication with the first body inlet port.

In some implementations, the ball is coupled to a rotatable switch for toggling the valve between the first and second positions. The switch is disposed external to the exterior surface of the valve.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Various implementations include an insufflation system for use with an endoscope. The insufflation system, according to some implementations, includes a housing, a $CO_2$ system, a water system, a foot pedal, and a control system. The housing defines an inlet $CO_2$ port and an outlet $CO_2$ port, and the housing includes an endoscope water pump. The $CO_2$ system includes outlet $CO_2$ port that couples a $CO_2$ conduit to an endoscope. The $CO_2$ conduit is disposed within the housing and couples the inlet and outlet $CO_2$ ports. The foot pedal is coupled to a control system, and the control system is electrically coupled to the endoscope water pump. The foot pedal is compressible, and compression of the foot pedal causes generation of an electrical signal that causes the endoscope water pump to turn on or off. The foot pedal has an outer surface that is at least partially illuminated.

In some implementations, the foot pedal of the insufflation system includes a compressible bladder with an outer surface including a phosphorescent material to illuminate the foot pedal. Other implementations of the compressible bladder foot pedal include an outer surface including a transparent or translucent material and a cavity within the compressible bladder which contains a light source such that the light emitted from the light source exits through the transparent or translucent material and illuminates the outer surface of the compressible bladder of foot pedal.

Figure 1:
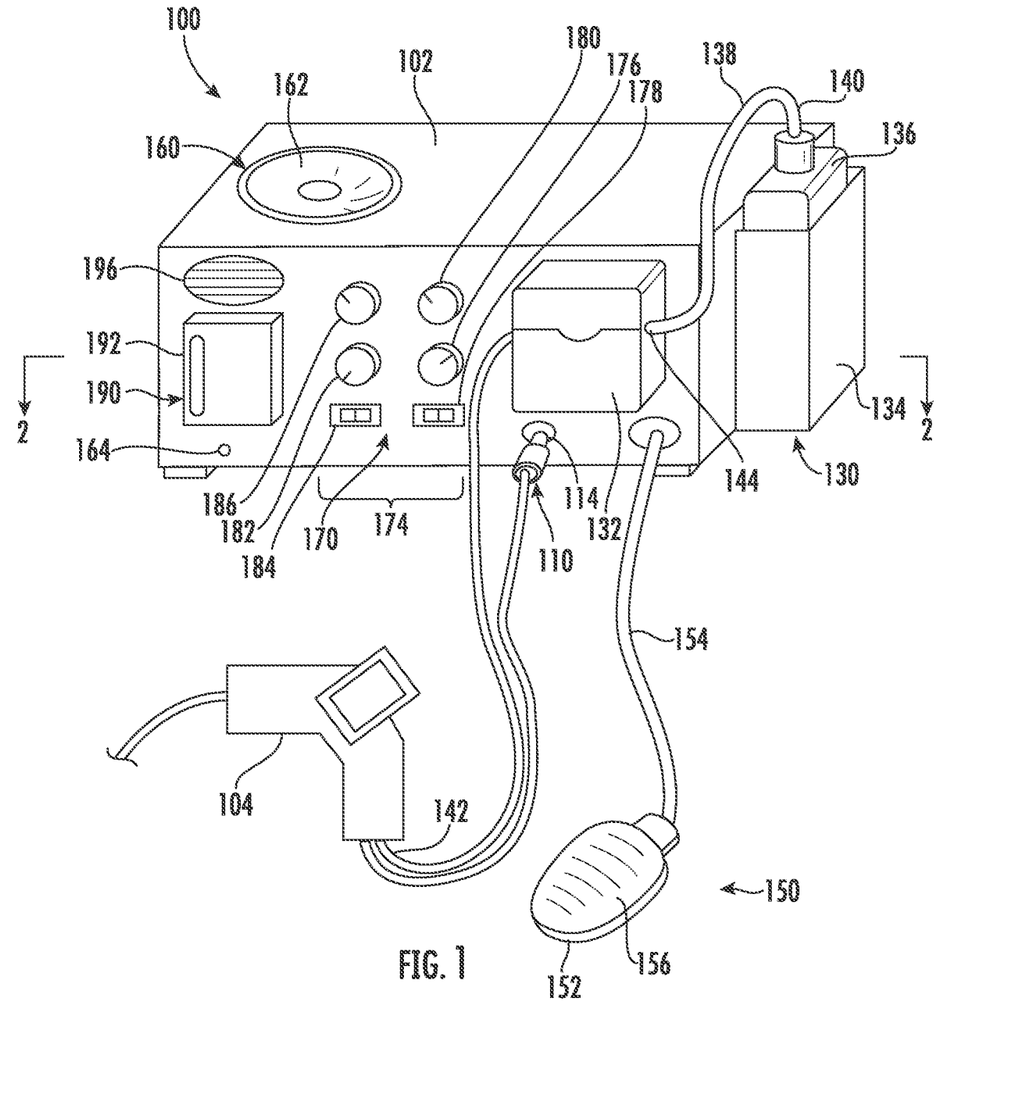
FIG. 1 is a perspective view of an insufflation system in accordance with one implementation.
Figure 2:
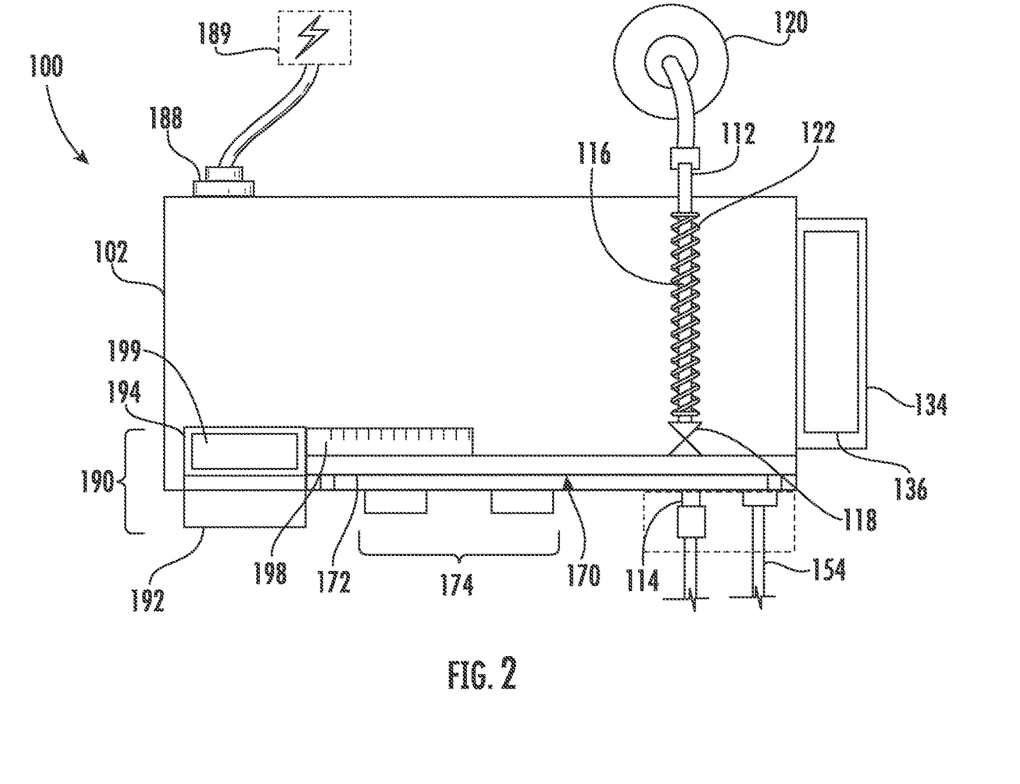
FIG. 2 is a cross sectional view of the insufflation system of FIG. 1 as viewed from the 2-2 line.

FIGS. 1 and 2 show one implementation of the insufflation system 100 with a housing 102, a $CO_2$ system 110, a water system 130, a foot pedal 150, a control system 170, an aromatic dispersion system 190, and an audio system 160. As shown in FIG. 2, the housing 102 defines an inlet $CO_2$ port 112 and an outlet $CO_2$ port 114. The housing 102 shown in FIGS. 1 and 2 and referred to herein is a single housing, but in other implementations, the housing could include multiple housings. The $CO_2$ system 110 further includes connectors in the inlet and outlet $CO_2$ ports 112, 114, a $CO_2$ conduit 116, a pressurized $CO_2$ source 120, and a $CO_2$ valve 118. A standard luer connector is disposed in the outlet $CO_2$ port 114, and a standard male threaded connector is disposed in the inlet $CO_2$ port 112. However, either connector could be a male or female connector, and any suitable connectors known in the art may be disposed within the outlet $CO_2$ port 114 and the inlet $CO_2$ port 112. Inside the housing 102, the connectors in the inlet $CO_2$ port 112 and the outlet $CO_2$ port 114 are coupled by the $CO_2$ conduit 116. The inlet $CO_2$ port 112 is coupled with the pressurized $CO_2$ source 120 for providing $CO_2$ to the inlet $CO_2$ port 112, and the outlet $CO_2$ port 114 is coupled to an endoscope 104. The $CO_2$ system 110 also includes the $CO_2$ valve 118 in fluid communication with the outlet $CO_2$ port 114 to control the flow of $CO_2$ through the $CO_2$ system 110. While FIG. 2 shows the $CO_2$ valve 118 located at the outlet $CO_2$ port 114, the $CO_2$ valve 118 can be located anywhere within the $CO_2$ system 110 (e.g., in the outlet $CO_2$ port 114, the inlet $CO_2$ port 112, the $CO_2$ conduit 116, the coupling between the $CO_2$ outlet and either the $CO_2$ source 120 or the endoscope 104) such that it can regulate the flow of $CO_2$ from the $CO_2$ source 120 to the endoscope 104. The $CO_2$ valve 118 shown in FIGS. 1 and 2 is a miniature proportional valve, but in other implementations, the $CO_2$ valve can be any other type of valve capable of varying the flow rate of $CO_2$ through the valve. The $CO_2$ source 120 is pressurized such that, when the $CO_2$ valve 118 is in an open position, $CO_2$ flows from the $CO_2$ source 120, through the $CO_2$ system 110, and out of the endoscope 104. The $CO_2$ system 110 also includes a trace heating system 122 thermally coupled to the $CO_2$ conduit 116 for heating the $CO_2$ flowing through the $CO_2$ conduit 116. The trace heating system 122 shown in FIG. 2 is an electric resistance heater, but in other implementations, the trace heating system is any other system capable of heating $CO_2$ flowing through the $CO_2$ conduit. The $CO_2$ source 120 shown in FIG. 2 is a metal tank containing compressed $CO_2$, but in other implementations, the $CO_2$ source is a device that compresses $CO_2$ or any other container containing compressed $CO_2$.

The water system 130 includes an endoscope water pump 132. In this implementation, the endoscope water pump 132 is disposed on an external surface of housing 102, but in other implementations, the water pump 132 may be disposed inside the housing 102. The endoscope water pump 132 is shown in FIG. 1 as a medical irrigation pump, but any suitable pump for use with endoscopic devices may be used. The water system 130 also includes a water container holder 134, a water container 136 disposed within the water container holder 134, and a water conduit 138. The water container holder 134 is mounted to the external surface of housing 102 and is designed to allow an operator to quickly and easily remove and replace the water container 136 disposed within the water container holder 134. For example, in this implementation, the water container holder 134 is an open-ended cup. A first end 140 of the water conduit 138 is coupled to the water container 136, and a second end 142 of the water conduit 138 is coupled to the endoscope 104. An intermediate portion 144 of the water conduit 138, which is between the first end 140 and the second end 142, is disposed within the endoscope water pump 132. The endoscope water pump 132 moves water from the water container 136, through the water conduit 138, and to the endoscope 104. In some implementations, the water container 136 is a medical grade endoscopy water container.

Figure 5:
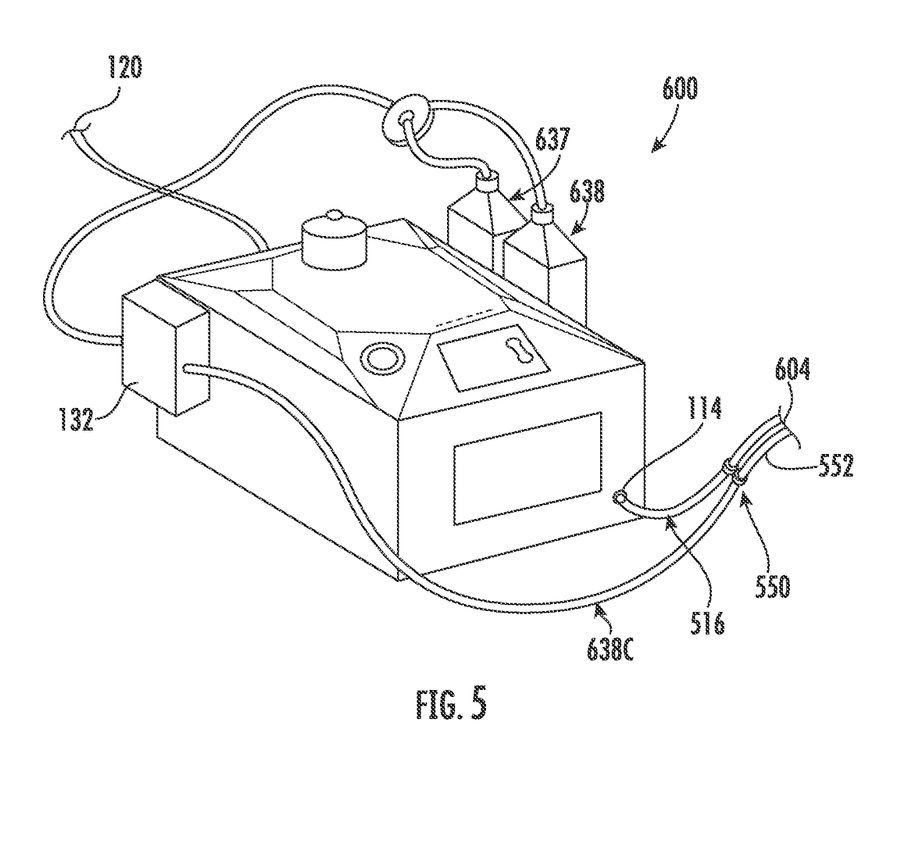
FIG. 5 illustrates an insufflation system according to another implementation.
Figure 6A:
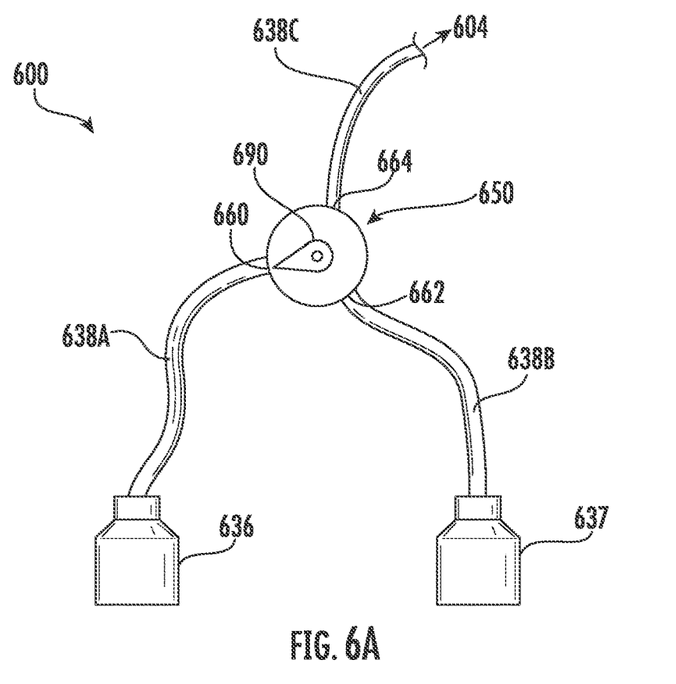
FIG. 6A illustrates a closer view of the valve and water conduits shown in FIG. 5.
Figure 6B:
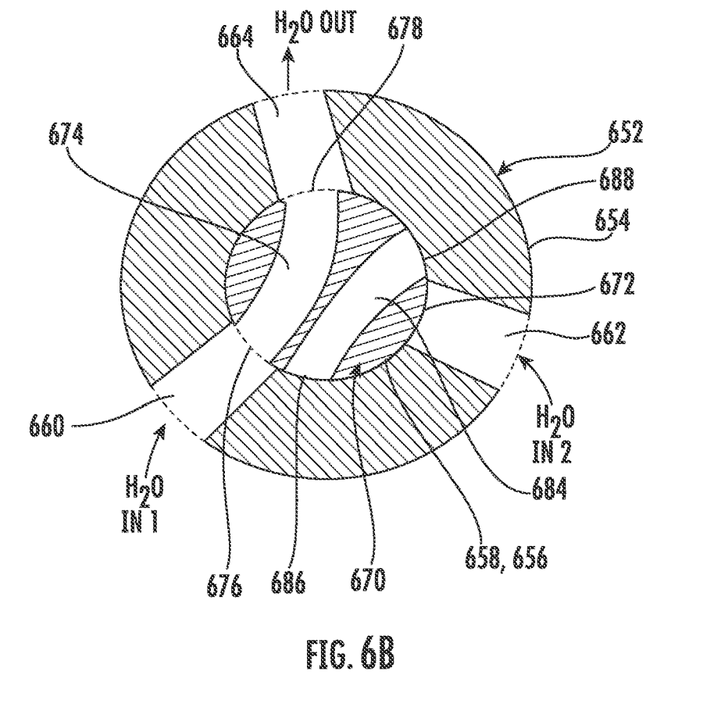
FIG. 6B illustrates a cross sectional view of the valve shown in FIG. 5.

The water system 130 of FIG. 1 shows a single water container holder 134, but in other implementations the water system 130 may include multiple water container holders 134 such that an operator can quickly and easily switch between the water container holders 134 providing water to the endoscope 104. Alternatively, multiple water containers 136 may be held within the water container holder 134. For example, FIGS. 5-6B illustrate an implementation that includes two water containers.

In some implementations, one or both of the $CO_2$ conduit 116 and the water conduit 138 are medical-grade tubing.

Figure 3A:
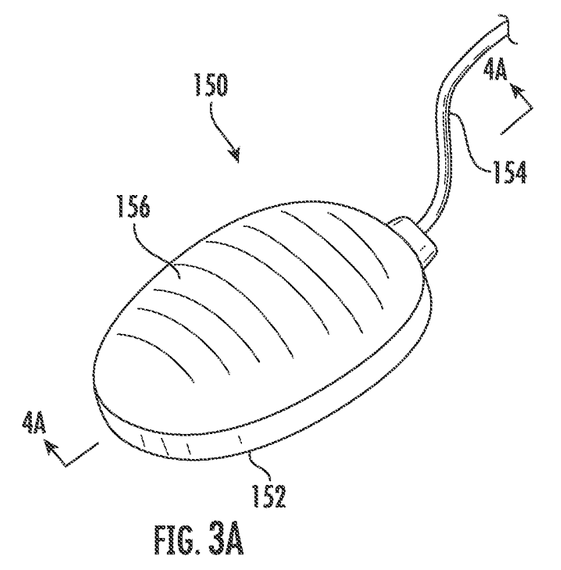
FIGS. 3A and 3B are two implementations of a foot pedal.
Figure 4A:
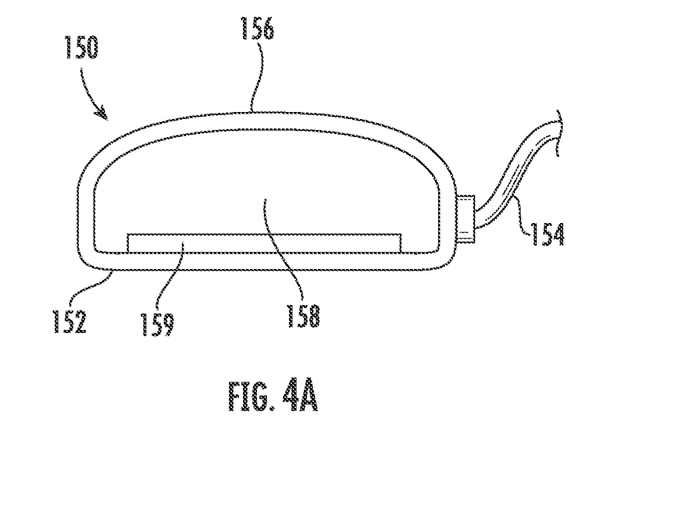
FIGS. 4A and 4B are cross sectional views of the foot pedals of FIG. 3A as viewed from line 4A-4A and 3B as viewed from line 4B-4B, respectively.
Figure 4B:
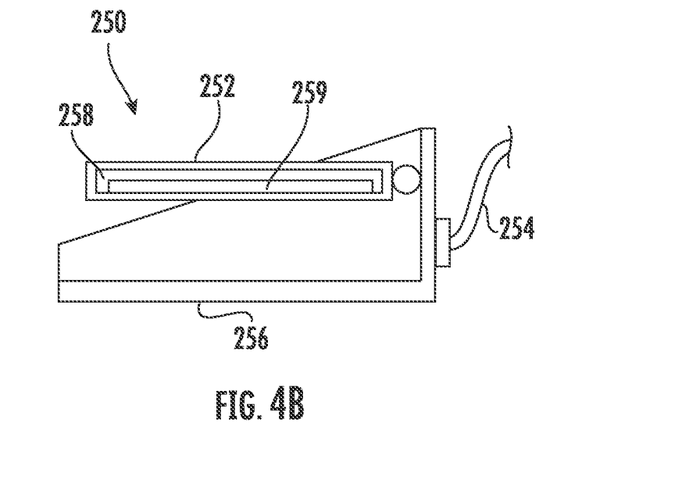

The foot pedal 150 includes a compressible bladder 152. The compressible bladder 152 is biased toward an expanded position and has an outer surface 156. The outer surface 156 of the compressible bladder 152 of the foot pedal 150 comprises a phosphorescent material to illuminate the foot pedal 150. For example, phosphorescent material may include, materials containing zinc sulfide, strontium aluminate, calcium sulfide, alkaline earth metal silicate, etc. Compression of compressible bladder 152 causes an electrical output signal to be received by the control system 170.

In other implementations, however, the outer surface 156 of the compressible bladder 152 is made of a transparent or translucent material. A light source 159 (e.g., LED(s)) for emitting visible light is located within a cavity 158 inside the compressible bladder 152 such that the light emitted from the light source 159 exits through the transparent or translucent material and illuminates the outer surface 156 of the compressible bladder 152 of the foot pedal 150.

Figure 3B:
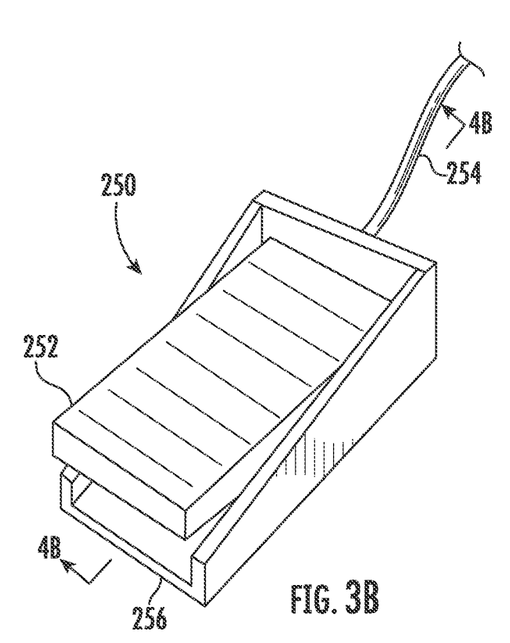

Although the foot pedal 150 shown in FIGS. 1 and 3A is a compressible bladder, the foot pedal 150 may instead include a hinge-type foot pedal 250 such as the one shown in FIG. 3B. FIG. 3B shows a foot pedal 250 with a stiff plate 252 that is hingedly coupled to a base plate 256. In this implementation, the stiff plate 252 can be made of phosphorescent material or can be made of a transparent or translucent material and be illuminated by a light source disposed adjacent the stiff plate 252. Compression of the stiff plate 252 toward the base plate 256 causes an electrical output signal to be received by the control system 170.

The control system 170 includes a circuit board 172, which is disposed within the housing 102. The circuit board 172 is electrically coupled (e.g., via a computer processor and memory that stores instructions for execution by the processor) to the $CO_2$ valve 118 to control the flowrate of $CO_2$ through the $CO_2$ valve 118 and to the endoscope water pump 132 to control water flow produced by the endoscope water pump 132. The circuit board 172 is further electrically coupled to control devices 174 and to the foot pedal 150. The circuit board 172 shown in FIG. 2 is a rigid, single sided, printed circuit board, but in other implementations, the circuit board is any other type of circuit board capable of receiving input signals from the control devices and sending output signals to components of the insufflation system.

When an operator compresses the foot pedal 150 toward a compressed position, an output signal is generated that causes water to flow to the endoscope 104. For example, in some implementations, the compressible bladder 152 may be coupled to an air pressure sensor that is electrically coupled, via one or more foot pedal wires 154, to the control system 170 for receiving and processing the electrical signal from the air pressure sensor. And, as another example, in some implementations, compression of the stiff plate 252 toward the base plate 256 causes generation of an electrical signal that is electrically communicated to the control system 170 via one or more foot pedal wires 254.

The electrical signal generated by the foot pedal 150 (e.g., bladder 152 or hinge-type foot pedal 252) is received by the circuit board 172 and is used to provide an "on" or "off" signal to the endoscope water pump 132. In this way, an operator can turn on and off the flow of water from the water system 130 to the endoscope 104 by compressing the foot pedal 150.

The control devices 174 are disposed on an external surface of the housing 102 and are adjustable by an operator to provide an electrical input signal to the circuit board 172. The control devices 174 include a water flow rate control device 176 for controlling a flow rate of the endoscope water pump 132 and a water switch 178 for providing an on/off signal to the endoscope water pump 132. The control devices 174 further include a water timer 180 electrically coupled to the water switch 178 for automatically providing an off signal to the endoscope water pump 132 after preset time period. The water switch 178 is electrically coupled to the foot pedal 150 via the control system 170 for receiving the on/off signal from compression of the foot pedal 150. The water switch 178 shown in FIG. 1 is an electrical rocker switch, but in other implementations, the water switch is a toggle switch, a push button switch, or any other switch capable of making and breaking an electrical connection in an electric circuit. The water flow rate control device 176 shown in FIG. 1 is a control dial, but in other implementations, the water flow rate control device is a slidable control switch, a data input device, or any other control device capable of generating a signal (e.g., variable signal) for controlling the water flow rate.

The control devices 174 also include a $CO_2$ flow rate control device 182 for controlling a flow rate through the $CO_2$ valve 118 and a $CO_2$ switch 184 for providing an on/off signal to the $CO_2$ valve 118. The control devices 174 further include a $CO_2$ timer 186 electrically coupled to the $CO_2$ switch 184 for automatically providing an off signal to the $CO_2$ valve 118 after preset time period. The control devices 174 in FIG. 1 are comprised of switches, buttons, and rotatable knobs, but any control device known in the art for providing an electrical input signal can be used. The housing 102 further defines a power port 188 to electrically couple the control system 170 to a power source 189 such that the circuit board 172 and other electronics can receive electric power. The $CO_2$ switch 184 shown in FIG. 1 is an electrical rocker switch, but in other implementations, the $CO_2$ switch is a toggle switch, a push button switch, or any other switch capable of making and breaking an electrical connection in an electric circuit. The $CO_2$ flow rate control device 182 shown in FIG. 1 is a control dial, but in other implementations, the $CO_2$ flow rate control device is a slidable control switch, a data input device, or any other control device capable of generating a signal (e.g., variable) for controlling the $CO_2$ flow rate.

The insufflation system 100 also includes an aromatic dispersion system 190. The aromatic dispersion system 190 includes an aroma source receptacle 192, an evaporative diffuser 194, and an aromatic outlet 196. An operator of the insufflation system 100 can insert an aroma source into the aroma source receptacle 192, which is disposed within the housing 102. The aroma source can be, for example, essential oil or any other suitable aroma source. The evaporative diffuser 194, also disposed within the housing 102, applies heat to the aroma source to diffuse the aroma source into the air inside the aromatic dispersion system 190. The aromatic outlet 196 is located on the housing 102 and allows the diffused aroma from the evaporative diffuser 194 to exit the insufflation system 100 to the surrounding environment. While the components of the aromatic dispersion system 190 of FIG. 1 are disposed within the housing 102, in some implementations, some or all of the components of the aromatic dispersion system 190 may be disposed outside of the housing 102.

In some implementations, the evaporative diffuser 194 of the aromatic dispersion system 190 includes a heatsink 198 and an absorbent pad 199. In this implementation, the aroma source is absorbed by the absorbent pad 199 located within the evaporative diffuser 194. The heatsink 198 draws heat from the control system 170 and/or any other electronic devices to heat and diffuse the aroma source within the absorbent pad 199.

The insufflation system 100 further includes an audio system 160. The audio system 160 includes a speaker 162 and an audio input receiver 164. The audio input receiver 164 and the speaker 162 are in communication with each other, and the audio input receiver 164 receives an audio input signal and transmits the signal to the speaker 162. The audio input receiver 164 and the speaker 162 are disposed within the housing 102, and the speaker 162 outputs the audio input signal as sound. While the speaker 162 and the audio input receiver 164 of FIG. 1 are in wired electrical communication, in some implementations, the speaker 162 and the audio input receiver 164 are in wireless electrical communication. Furthermore, the audio input receiver 164 can define an electrical input port for receiving a plug coupled to a wire(s) carrying the audio input signal or the audio input receiver 164 can be a BLUETOOTH communication device such that it can receive the audio input signal wirelessly.

Figure 7:
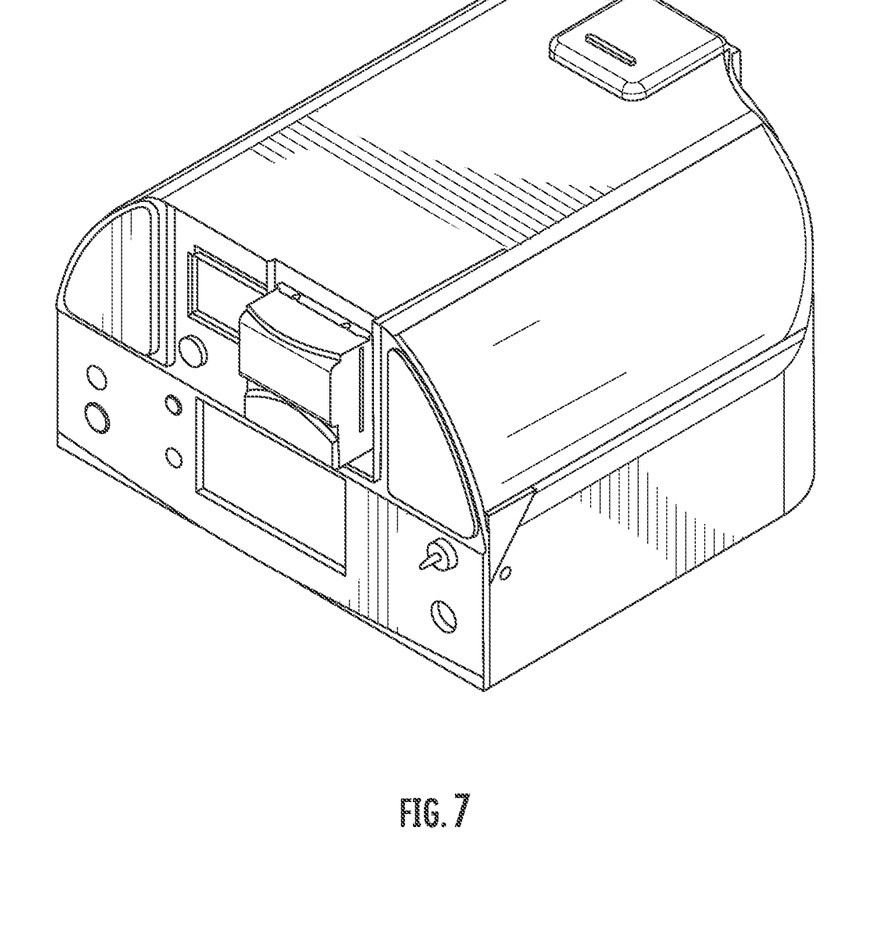
FIG. 7 is a perspective view of an insufflation system according to another implementation.
Figure 8:
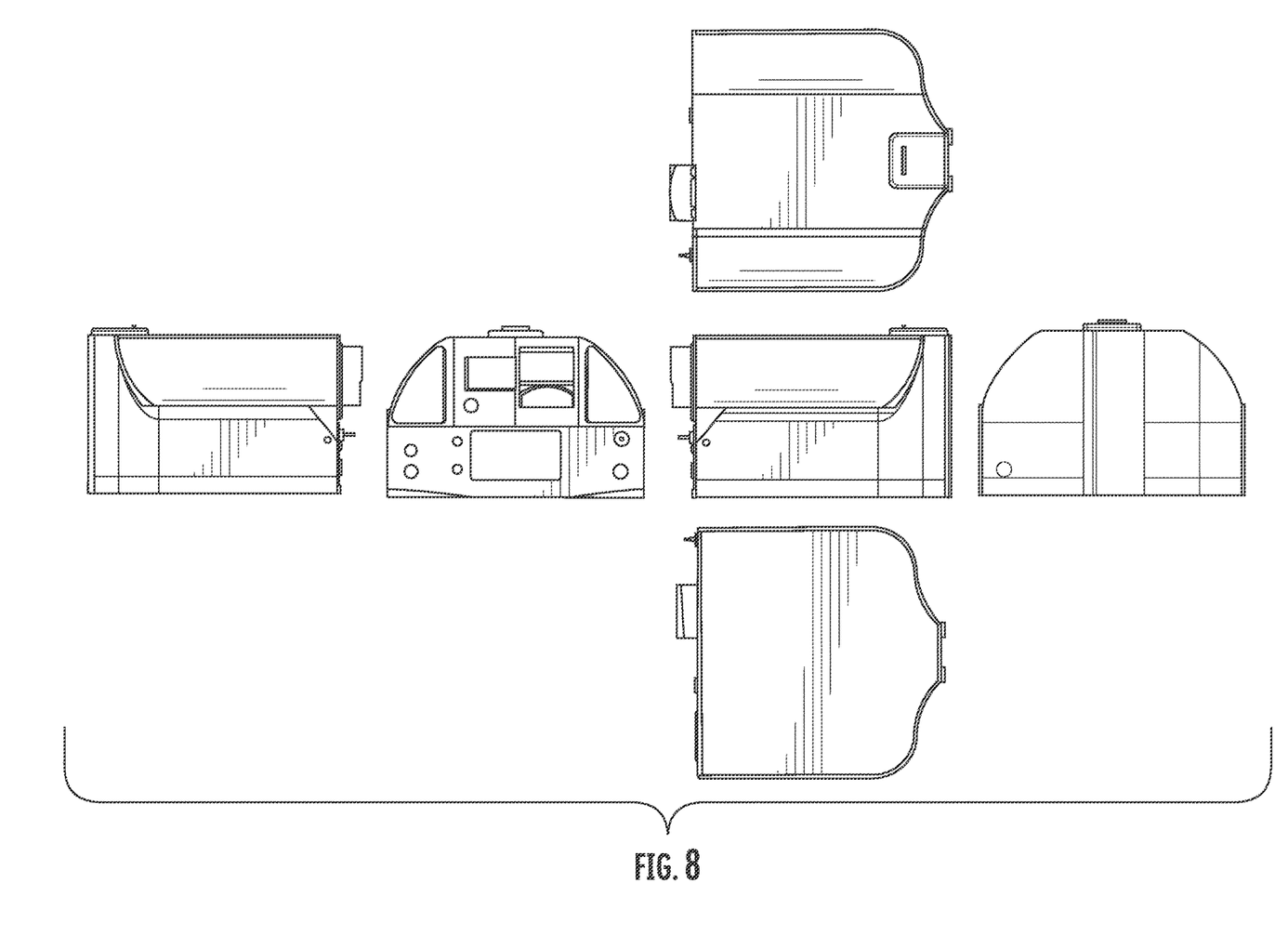
FIG. 8 illustrates orthographic views of the front side, back side, left side, right side, top, and bottom of the insufflation system of FIG. 7.

FIGS. 7 and 8 show another implementation of the housing of an insufflation system similar to the insufflation system 100 of FIGS. 1 and 2.

FIG. 5 illustrates an insufflation system 600 that is similar to the system 100 described above in relation to FIGS. 1-4B. However, in system 600, the outlet conduits 638C, 516 are coupled together with a clip 550, and the system 600 includes two water containers 636, 637 that are coupled to a valve for controlling which water containers 636, 637 provides water to the endoscope 604.

As shown in FIG. 5, the clip 550 has a retaining portion 552 that couples a portion of the $CO_2$ conduit 516 and a portion of the water conduit 638C. The clip 550 couples the two conduits 638C, 516 to prevent the conduits 638C, 516 from becoming tangled when the insufflation system 600 is used by an operator.

FIG. 6A shows a close-up of the two water containers 636, 637 and valve 650 shown in FIG. 5, and FIG. 6B shows a cross sectional view of the valve 650. The valve 650 includes a body 652 and a ball 670. The body 652 has an exterior surface 654 and an interior seat 658 having an interior surface 656. The body 652 also includes a body outlet port 664, a first body inlet port 660, and a second body inlet port 662, all of which are in fluid communication with the interior surface 656 of the seat 658 and extend to the exterior surface 654 of the body 652.

The ball 670 of the valve 650 has an outer surface 672 and is disposed within the seat 658 such that the ball 670 can be rotated. The ball 670 defines at least a first arcuate passage 674 and a second arcuate passage 684 which are separate from, and do not intersect, each other. The first passage 674 extends from a first ball inlet 676 defined by the outer surface 672 of the ball 670 to a separate, first ball outlet 678 defined by the outer surface 672 of the ball 670. Similarly, the second passage 684 extends from a second ball inlet 686 defined by the outer surface 672 of the ball 670 to a separate, second ball outlet 688 defined by the outer surface 672 of the ball 670.

As shown in FIG. 6A, one of the two water containers 636 is coupled to the first body inlet port 660 by a first water conduit 638A. Similarly, the other of the two water containers 637 is coupled to the second body inlet port 662 by a second water conduit 638B. A third water conduit 638C couples the body outlet port 664 to the endoscope 604.

As mentioned above, the ball 670 is rotatable within the seat 658 of the valve body 652. The arcuate passages 674, 684 are arranged such that, when the ball 670 is in a first position, the first ball inlet 676 of the first passage 674 is aligned with the first body inlet port 660 and the first ball outlet 678 is aligned with the body outlet port 664. And, the second ball inlet 686 of the second passage 684 is not aligned or in fluid communication with the second body inlet port 662 when the ball 670 is in the first position. Thus, in the first position, the first passage 674 is in fluid communication with the first body inlet portion 660 and the body outlet portion 664, and water from the first water container 636 can flow to the endoscope 604. When the ball 670 is rotated within the valve seat 658 to a second position, the second ball inlet 686 of the second passage 684 is aligned with the second body inlet port 662 and the second ball outlet 688 is aligned with the body outlet 664. And, the first ball inlet 676 of the first passage 674 is not aligned or in fluid communication with the first body inlet port 660 when the ball 670 is in the second position. Thus, in the second position, the second passage 684 is in fluid communication with the second body inlet portion 662 and the body outlet portion 664, and water from the second water container 637 can flow to the endoscope 604. While the valve 650 shown in FIGS. 6A and 6B include a spherical "ball" 670, any shape "ball" can be used that is capable of rotating within the interior seat of the body, for example, cylindrical, conical, etc.

As shown in FIG. 6A, the valve 650 also includes a rotatable external switch 690 that is coupled to the outer surface 672 of the ball 670 for manually toggling the position of the ball 670 between the first and second positions. By utilizing the valve 650, an endoscope operator can easily and quickly switch between water containers 636, 637 to minimize the stoppage time for changing water containers during an endoscopy procedure. In addition, various implementations utilizing one or more combinations of the above features minimize the physical space occupied by individual pieces of equipment.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An insufflation system, the system comprising:
  a housing defining an inlet $CO_2$ port and an outlet $CO_2$ port;
  a $CO_2$ conduit disposed within the housing that couples the inlet $CO_2$ port and the outlet $CO_2$ port;
  an endoscope water pump coupled to the housing;
  a foot pedal coupled to a control system, the control system being electrically coupled to the endoscope water pump and the housing, and the foot pedal being compressible, wherein compression of the foot pedal causes generation of an electrical signal that causes the endoscope water pump to turn on or off, and the foot pedal has an outer surface that is at least partially illuminated;
  a valve configured for selecting a water container from two or more water containers for providing water to an endoscope; and
  an aromatic dispersion system, wherein the housing defines an aromatic outlet being coupled with the aromatic dispersion system, the aromatic dispersion system comprising an aroma source receptacle and an evaporative diffuser for diffusing an aroma source in the aroma source receptacle, wherein the diffused aroma source flows through the aromatic outlet to an environment outside of the housing.

2. The insufflation system of claim 1, wherein at least one of the two or more water containers is coupled to the housing.

3. The insufflation system of claim 1, the system further comprising:
  a $CO_2$ valve in fluid communication with the outlet $CO_2$ port; and
  at least one circuit board disposed within the housing, the at least one circuit board being electrically coupled to the $CO_2$ valve and the endoscope water pump to control a flow rate of $CO_2$ through the $CO_2$ valve and water flow through the endoscope water pump.

4. The insufflation system of claim 1, wherein at least a portion of the aromatic dispersion system is disposable within the housing.

5. The insufflation system of claim 1, wherein the aroma source is essential oil.

6. The insufflation system of claim 1, wherein the evaporative diffuser comprises a heatsink disposed within the housing for evaporating the aroma source disposed within an absorbent pad.

7. The insufflation system of claim 1, further comprising at least one speaker and an audio input receiver disposed within the housing, the audio input receiver for receiving an audio input signal, wherein the audio input receiver is in electrical communication with the at least one speaker, and the audio input signal is output by the at least one speaker.

8. The insufflation system of claim 7, wherein the audio input receiver is in wireless communication with an audio input source to receive the audio input signal.

9. The insufflation system of claim 8, wherein the audio input receiver comprises a BLUETOOTH communication device.

10. The insufflation system of claim 1, further comprising a trace heating system thermally coupled to the $CO_2$ conduit.

11. The insufflation system of claim 1, wherein the outer surface of the foot pedal comprises a phosphorescent material.

12. The insufflation system of claim 1, wherein the outer surface of the foot pedal comprises a transparent or translucent material, and the foot pedal comprises a light source that emits visible light through the transparent or translucent material.

13. The insufflation system of claim 1, the valve comprising:
  a body having an exterior surface and defining an interior seat having an interior surface, a body outlet port, and at least a first body inlet port and a second body inlet port, the body outlet port, the first body inlet port, and the second body inlet port extending from the exterior surface to the interior surface of the interior seat; and
  a ball having an outer surface and being disposed within the interior seat, the ball defining at least a first passage and a second passage therethrough, each of the first passage and the second passage being arcuate and having a ball inlet and a ball outlet defined by the outer surface of the ball, the ball inlet and the ball outlet of each of the first passage and the second passage being spaced apart from each other, wherein the first passage and the second passage do not intersect, and wherein the ball is rotatable within the interior seat between a first position and a second position;
  wherein in the first position, the ball inlet of the first passage is aligned with the first body inlet port and the ball outlet of the first passage is aligned with the body outlet port and the ball inlet of the second passage is not in fluid communication with the second body inlet port, and
  wherein in the second position, the ball inlet of the second passage is aligned with the second body inlet port and the ball outlet of the second passage is aligned with the body outlet port and the ball inlet of the first passage is not in fluid communication with the first body inlet port.

14. The insufflation system of claim 13, wherein the two or more water containers comprise a first water container and a second water container, the system further comprising a first water conduit, a second water conduit, and a third water conduit, the first water conduit for coupling the first body inlet port to the first water container, the second water conduit for coupling the second body inlet port to the second water container, and the third water conduit for coupling the endoscope to the body outlet port.

15. The insufflation system of claim 14, further comprising the endoscope for being coupled to a $CO_2$ source and the first water container and the second water container, the endoscope being couplable to the $CO_2$ source via the inlet $CO_2$ port and the outlet $CO_2$ port and the $CO_2$ conduit, and the endoscope being couplable to the first water container and the second water container via the first water conduit, the second water conduit, and the third water conduit, the body outlet port, the first body inlet port and the second body inlet port, the valve, and the third water conduit extending through the endoscope water pump.

16. The insufflation system of claim 15, wherein the $CO_2$ conduit and the third water conduit are coupled together using a clip.

17. The insufflation system of claim 13, wherein the ball is coupled to a rotatable switch for toggling the valve between the first position and the second position, the rotatable switch being disposed external to the exterior surface of the body of the valve.

18. The insufflation system of claim 1, wherein the foot pedal comprises a compressible bladder.

19. The insufflation system of claim 1, wherein the foot pedal includes a stiff plate that is hingedly coupled to a base plate, and compression of the stiff plate toward the base plate generates the electrical signal.

* * * * *